United States Patent [19]
Turtzo

[11] Patent Number: 6,099,490
[45] Date of Patent: Aug. 8, 2000

[54] SUPPORT BRACE

[76] Inventor: Craig H. Turtzo, 2637 Westview Ct., Clearwater, Fla. 33761

[21] Appl. No.: 09/182,051

[22] Filed: Oct. 29, 1998

[51] Int. Cl.⁷ .................................. A61F 5/00; A41F 9/00
[52] U.S. Cl. .................................................. 602/19; 2/311
[58] Field of Search .......................... 602/19, 5; 450/155; 2/44, 311, 312, 317–319; 128/96.1, 112.1, 100.1, 102.1

[56] References Cited

U.S. PATENT DOCUMENTS

| | | |
|---|---|---|
| 70,683 | 11/1867 | Baker ............................... 128/100.1 |
| 1,075,348 | 10/1913 | Fritsch . |
| 1,184,581 | 5/1916 | Sigurini .............................. 450/121 |
| 2,541,487 | 2/1951 | Triplett . |
| 2,813,526 | 11/1957 | Beebe . |
| 2,828,737 | 4/1958 | Hale . |
| 4,459,979 | 7/1984 | Lewis, Jr. . |
| 4,475,543 | 10/1984 | Brooks et al. . |
| 5,046,488 | 9/1991 | Schiek . |
| 5,105,806 | 4/1992 | Woodhouse et al. . |
| 5,179,942 | 1/1993 | Drulias et al. . |
| 5,207,636 | 5/1993 | Striono . |
| 5,226,874 | 7/1993 | Heinz et al . |
| 5,232,424 | 8/1993 | Pearson et al. . |
| 5,257,419 | 11/1993 | Alexander . |
| 5,259,831 | 11/1993 | LeBron . |
| 5,267,947 | 12/1993 | James et al. . |
| 5,267,948 | 12/1993 | Elliott . |
| 5,310,401 | 5/1994 | Striono . |
| 5,334,134 | 8/1994 | Saunders .............................. 602/19 |
| 5,346,461 | 9/1994 | Heinz et al. . |
| 5,363,863 | 11/1994 | Lelli et al. . |
| 5,489,260 | 2/1996 | Striano . |
| 5,500,959 | 3/1996 | Yewer, Jr. . |
| 5,569,171 | 10/1996 | Muncy . |
| 5,632,723 | 5/1997 | Grim . |
| 5,632,724 | 5/1997 | Lerman et al. . |
| 5,634,891 | 6/1997 | Beczak, Sr. et al. . |
| 5,690,609 | 11/1997 | Heinz . |

OTHER PUBLICATIONS

Bio Cybernetics International Cybertech 1000 advertisement, 1998.

*Primary Examiner*—Stephen R. Crow
*Assistant Examiner*—Denise Pothier
*Attorney, Agent, or Firm*—Greensfeuder, Hemker & Gale, P.C.

[57] ABSTRACT

A support brace having a generally contoured lumbar support section and an abdominal support system, comprising an abdominal support pad elastically connected to a lateral edge of the lumbar support member and an elastic abdominal support band attached to the opposite lateral edge of the lumbar support member, and also having two inelastic straps, each being independently attached to an opposite lateral edge of the lumbar support member. The lumbar support member has a first and a second D-ring attached to its outer surface, and the abdominal support pad and the abdominal support band have single D-rings attached to their outer surfaces. The straps are independently threaded through the abdominal support system's D-ring and then turned back and threaded through the D-rings of the lumbar support member. The support brace is selectively tightened by pulling on the ends of the straps and cinching the brace to the optimal tightness, while maintaining the desired compression about the wearer's mid-section.

27 Claims, 7 Drawing Sheets

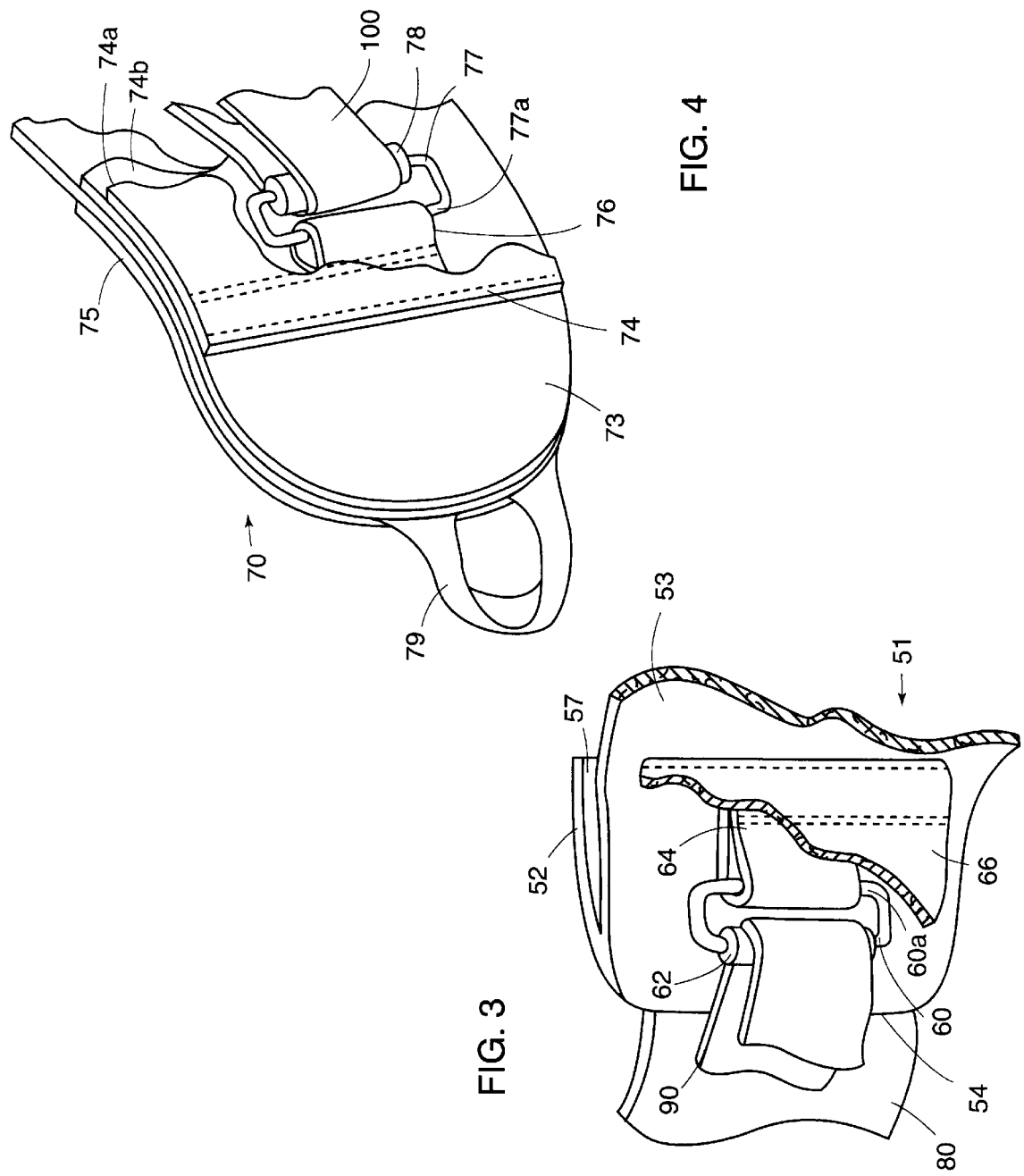

SUPPORT BRACE

FIELD OF THE INVENTION

The present invention relates generally to the field of orthotic devices, and, more specifically, to lower back and abdominal braces united by a double D-ring tightening system for securing and cinching the brace which allows the wearer to quickly and easily tighten the brace to the desired compression unassisted and without the aid of others.

BACKGROUND OF THE INVENTION

Individuals suffering from low back pain caused by musculoskeletal dysfunction can benefit from the use of back braces that stabilize the lumbar spine by limiting anterior/posterior and/or medial/lateral movement. There are a multitude of braces and supports used for this purpose. The braces typically include a rigid or semi-rigid back section belted to the wearer. For instance, a very rigid back support might be prescribed after back surgery to absolutely limit spinal movement to promote the healing process. Less rigid materials would be used, for instance, to permit some movement but at the same time provide some support of the lumbar spine. Belts with a buckle or hook and loop-type fastener material are typically used to tighten and to secure the brace about the wearer's mid-section. Thus worn, back braces offer support and limitation of movement aimed at the underlying pathology of the wearer.

Additionally, it is well known that an increase in the compression of an individual's abdominal area will result in a decrease in compression of their lumbar spine. As such, compression of the lumbar spine into the back portion of a brace by lifting and pulling an abdominal section into a wearer's abdomen offers some decompression of the lumbar spine and will tend to reduce associated lower back pain. Unfortunately, many of the back braces available today do not have an abdominal support member. Those presently available braces that do provide an abdominal support member do not allow the wearer to alter the support given by the brace, thus limiting the flexibility of the wearer and his or her treatment modality.

Additionally, presently available braces have met with limited success because they are, for the most part, cumbersome to put on and take off. Moreover, such braces are difficult, if not impossible, to tighten and secure by an infirm patient suffering from low-back pain. Many braces require their wearers to have assistance cinching the braces to the desired compression. As such, patient compliance with the prescribed use of back braces is less than ideal.

Many of the presently available braces have various pieces of exposed hardware used for tightening or fastening which can irritate or chafe the wearer's skin. The exposed hardware can also make donning and wearing such braces difficult due to the propensity of the exposed hardware to catch or snag on articles of clothing and other items thus limiting the utility of the brace. There remains a need for an improved lumbar support system that can be easily donned and cinched by the wearer without the aide of others that will not be susceptible to snagging on the wearer's clothing or other items.

Accordingly, problems associated with the known art include: (1) difficulty in donning and doffing the brace; (2) difficulty in cinching the brace due to the wearer's inability to tighten the brace by his or her own efforts; (3) exposed fastening and tightening hardware; and (4) the lack of sufficient abdominal support. The following art provides examples:

U.S. Pat. No. 5,690,609, which issued to Heinze, III, discloses a compound brace with a two-piece abdominal support pad and a back support pad. The brace also contains a multi-belt tightening system that loops the belts through various slots in the back support pad and the abdominal support pads. The back and abdominal support pads are secured and tightened about the wearer by pulling the ends of the outer belt and fastening the ends to the device with hook and loop fastener material. However, the wearer is required to pull the outer tightening belt ends in an awkward direction for the wearer, especially when the wearer suffers from low back pain or other physical infirmity. Moreover, the Heinze, III brace is difficult to cinch to the desired compression. The tightening belt passes through slots in the stiff brace members, which cause friction and tend to limit the wearer's ability to cinch the brace tightly around his or her mid-section. Because the slots in the support pads are exposed, the wearer's clothing can become entangled in the slots, limiting the brace's usefulness.

Similarly, Lelli, et al., U.S. Pat. No. 5,363,863, discloses a lumbar support belt with a back pad and a two-piece abdominal support section. However, this device fails to overcome the problem associated with donning and doffing the brace by a wearer with limited physical strength without the assistance of another. In order to adequately compress the brace, the wearer must have sufficient physical strength to buckle the abdominal support pads together.

The Striano U.S. Pat. No. 5,489,260 features a brace with a posterior shell and a flexible fabric support belt to secure the brace about the wearer. This simple structure does not, however, provide for abdominal support to aid in the effectiveness of the brace. Additionally, the cinching hardware of the device disclosed by Striano can become entangled by the wearer's clothing during donning.

The Muncy U.S. Pat. No. 5,569,171 features a simple two-piece device intended to preclude rotation of the wearer's lumbar spine. Although the Muncy brace includes an abdominal support member, it does not facilitate problems associated with self-securing the brace by the wearer.

Although the art reveals braces that provide support to the wearer's abdominal region, none are structured as in the present device, for providing stiffeners of varying rigidity to accommodate the wearer's specific compressive needs. Examples include the following:

The patent which issued to Beczak, Sr., et al., U.S. Pat. No. 5,634,891, shows a corset-type orthotic device which, although having an abdominal section, does not provide a structure to adjustably support the abdomen of the wearer with a rigid or semi-rigid member.

Pearson, et al., U.S. Pat. No. 5,232,424, provides a flexible cushion in an abdominal section, but does not allow for varying the degree of abdominal support or varying the range of a wearer's motion by altering the rigidity of the abdominal support member.

The Heinze III and Lelli, et al. devices, noted above, provide multi-piece abdominal support sections, but neither device allows the wearer to selectively alter the rigidity of the abdominal section.

By contrast, the device of the present invention is designed to permit the wearer to put on and take off the brace with ease and to cinch the support members of the device to the desired compression without the aid of others, a mode heretofore unknown. The combination of the double D-ring tightening system and the abdominal support member ensure ease of use of the brace, especially for wearers of limited strength due to low-back pain or other infirmity. This combination of easy donning and unassisted tightening ensures patient compliance, thus aiding the healing process. An additional benefit of the present invention is that the D-rings used to cinch the device are covered to prevent entanglement with the wearer's clothing or other items. Further, the cloth casing of the brace can be easily cleaned and washed.

SUMMARY OF THE INVENTION

In order to overcome the shortcomings of known lumbar support braces, the present invention has been developed with several goals in mind. The device features a number of advantages, key among which is the adaptation of a double D-ring configuration for cinching the device to the wearer's desired tightness. D-rings strategically placed on the lumbar support section and the abdominal support system allows the wearer to use a reduced amount of force to compress the brace about the wearer's mid-section. The D-rings, when used in tandem, work like a block and tackle and create a mechanical advantage to the wearer for cinching the brace by pulling the lumbar support section and the abdominal support system towards one another. Thus, the support brace allows a person of limited physical strength to cinch the brace to its desired tightness without the aid of others, thereby instilling a degree of freedom and confidence to the wearer and insuring compliance with a physician's wearing instructions.

It is further among the features of the present invention, having the advantages thus indicated, that the abdominal section of the new device be formed as to accommodate stiffeners of varying rigidity. The more rigid the stiffener used by the wearer in the abdominal section, the greater compression of the abdominal cavity the wearer can achieve, in turn decompressing the wearer's lumbar spine. Additionally, the abdominal support stiffeners limit the wearer's range of motion, facilitating the healing process.

It is further among the features of the present invention, having the advantages thus indicated, that the hardware used to facilitate the cinching of the brace be covered so that it does not become entangled in the wearer's clothing or on other items. The D-rings, noted above, are covered in such a fashion that the covering does not impede the utility of the D-rings or the mechanical advantage provided thereby.

The above features result in a support brace that provides for comfortable and easy wearing. The construction of the new brace facilitates the ease of donning and cinching the device to the desired tightness by the wearer without the need of assistance from others, which also aids in patient compliance with using the brace.

Accordingly, in furtherance of the above features and advantages, the present device is, briefly, a support brace having a generally contoured lumbar support section and an abdominal support system, comprising an abdominal support pad elastically connected to a lateral edge of the lumbar support section and an elastic abdominal support band attached to the opposite lateral edge of the lumbar support section. The brace also has two inelastic straps, each being independently attached to an opposite lateral edge of the lumbar support section. The lumbar support section has a first and a second D-ring attached either to the outer plate of a lumbar support laminate member or to its outer surface, and the abdominal support pad and the abdominal support band have single D-rings attached to their outer surfaces. The D-rings are covered with material or fabric in such a manner as to not impair their function. The first strap is threaded through the abdominal support pad's D-ring and then turned back and threaded through the first D-ring of the lumbar support section. Similarly, the second strap is first threaded through the abdominal support band D-ring and then through the second lumbar support D-ring.

The brace can be easily donned by placing the lumbar support section against the wearer's lower back and wrapping the abdominal support pad and abdominal support band around the wearer's mid-section and fastening them together by VELCRO®, thus forming the abdominal support system. The support brace is selectively tightened by pulling on the ends of the straps and cinching the brace to the optimal tightness, and maintaining the desired compression about the wearer's mid-section by fastening the straps to the formed abdominal support system with VELCRO® or other fasteners.

Other features and advantages will be, in part, apparent and, in part, pointed out below.

BRIEF DESCRIPTION OF THE DRAWINGS

FIG. 3 is a front view of the abdominal support pad of FIG. 2, partially broken away to illustrate the attachment of a D-ring to the abdominal support pad and its hidden nature.

FIG. 4 is a front perspective view of the abdominal support band of FIG. 2, partially broken away to illustrate the attachment of a D-ring to the abdominal support band and its hidden nature.

Throughout the drawings, like parts will be indicated by like element numbers. For simplicity in the figures, in some views some of the parts of the brace are not shown.

DESCRIPTION OF PRACTICAL EMBODIMENTS

Figure 1:
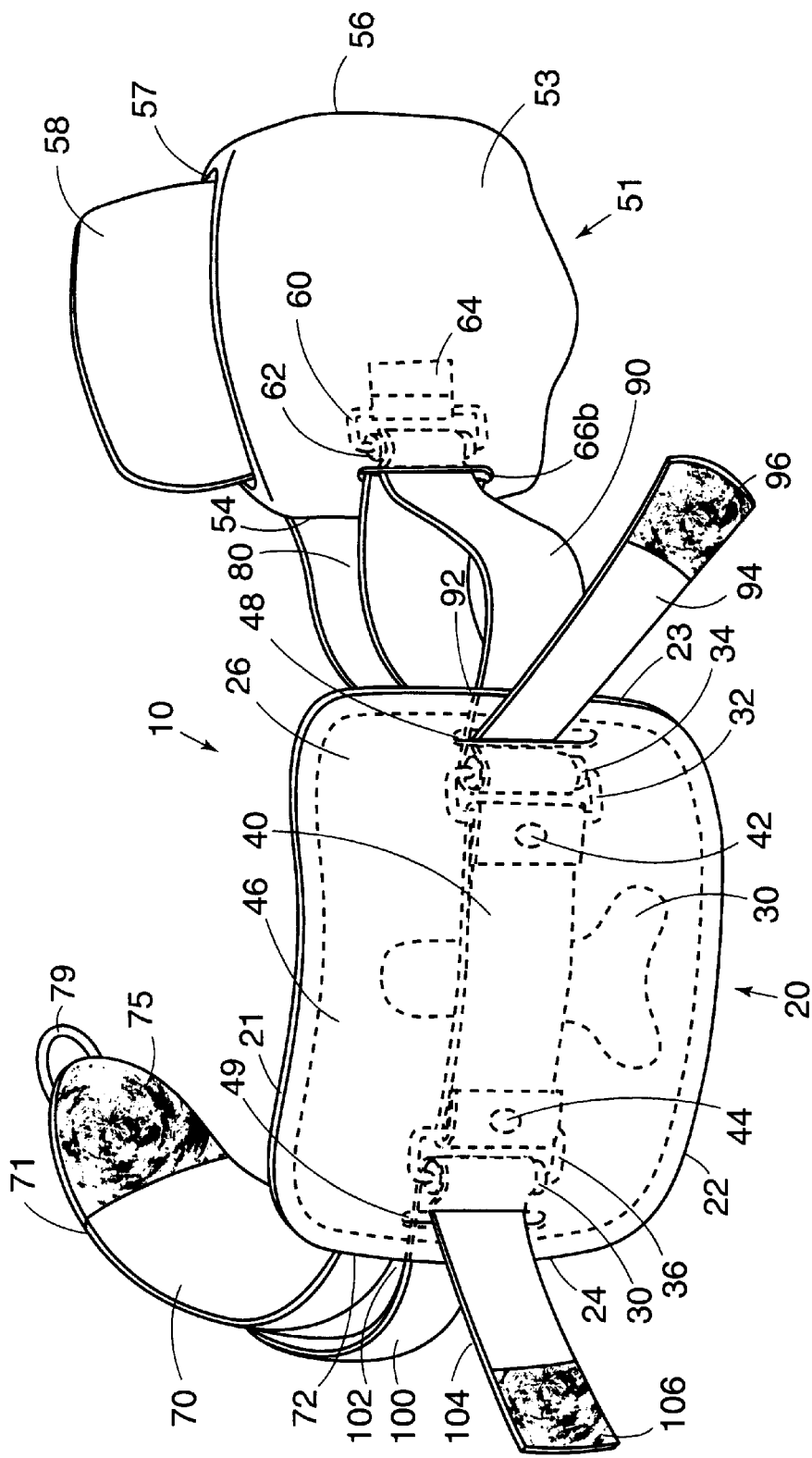
FIG. 1 is a rear perspective view of the support brace, shown open and having an abdominal stiffener extending from an abdominal support pad. Certain hidden features are shown in phantom.
Figure 2:
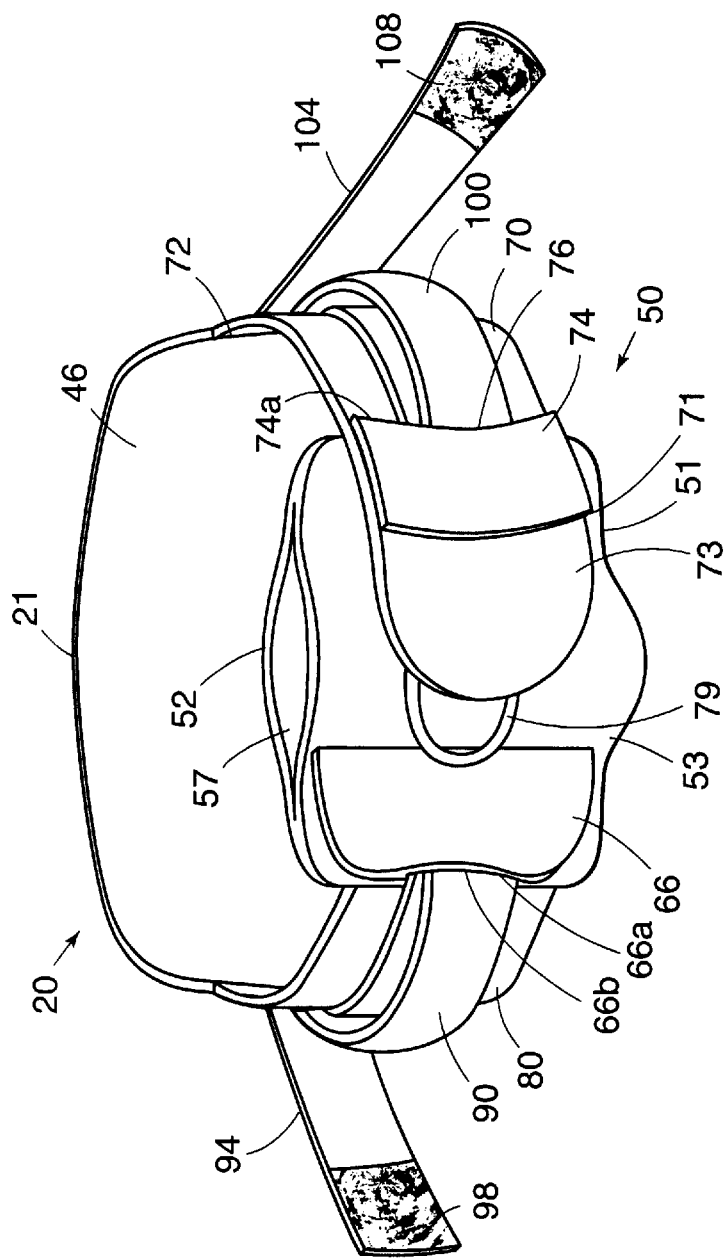
FIG. 2 is a front perspective view of the support brace of FIG. 1, shown closed with the abdominal support pad and abdominal support band joined to form the abdominal support system.

With reference to the drawings, and especially FIGS. 1 and 2, 10 generally designates a lumbar support brace (or support brace) consisting generally of a lumbar support section 20, an abdominal support system 50, a band 80 and first and second straps 90 and 100, respectively. The abdominal support system 50 is comprised generally of the abdominal support pad 51 and the abdominal support band 70, as are shown in a joined position in FIG. 2. As more fully described below, the lumbar support section 20 is joined on one side to the abdominal support pad 51 by band 80. Abdominal support band 70 is attached at the opposite side of lumbar support section 20 from band 80 and wraps around the wearer's torso to detachably fasten to abdominal support pad 51. Straps 90 and 100 are used to selectively tighten the brace around the wearer's mid-section. An optional abdominal stiffener member 58 is shown protruding from abdominal support pad 51 in FIG. 1, and is provided to aid in the support given by the support brace 10 when donned by the wearer.

Figure 6:
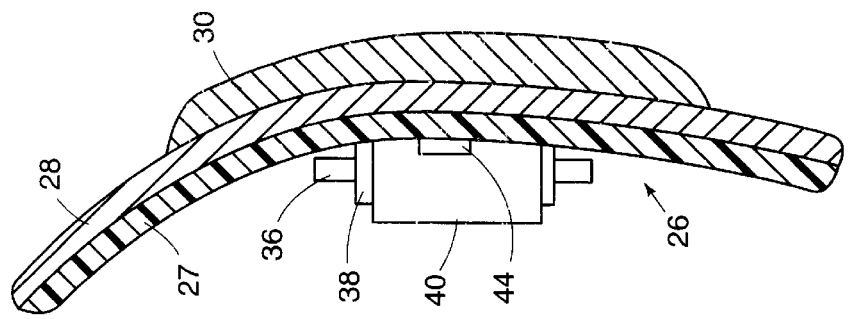
FIG. 6 is a sectional view of the lumbar support member taken along line 6—6 of FIG. 5.
Figure 5:
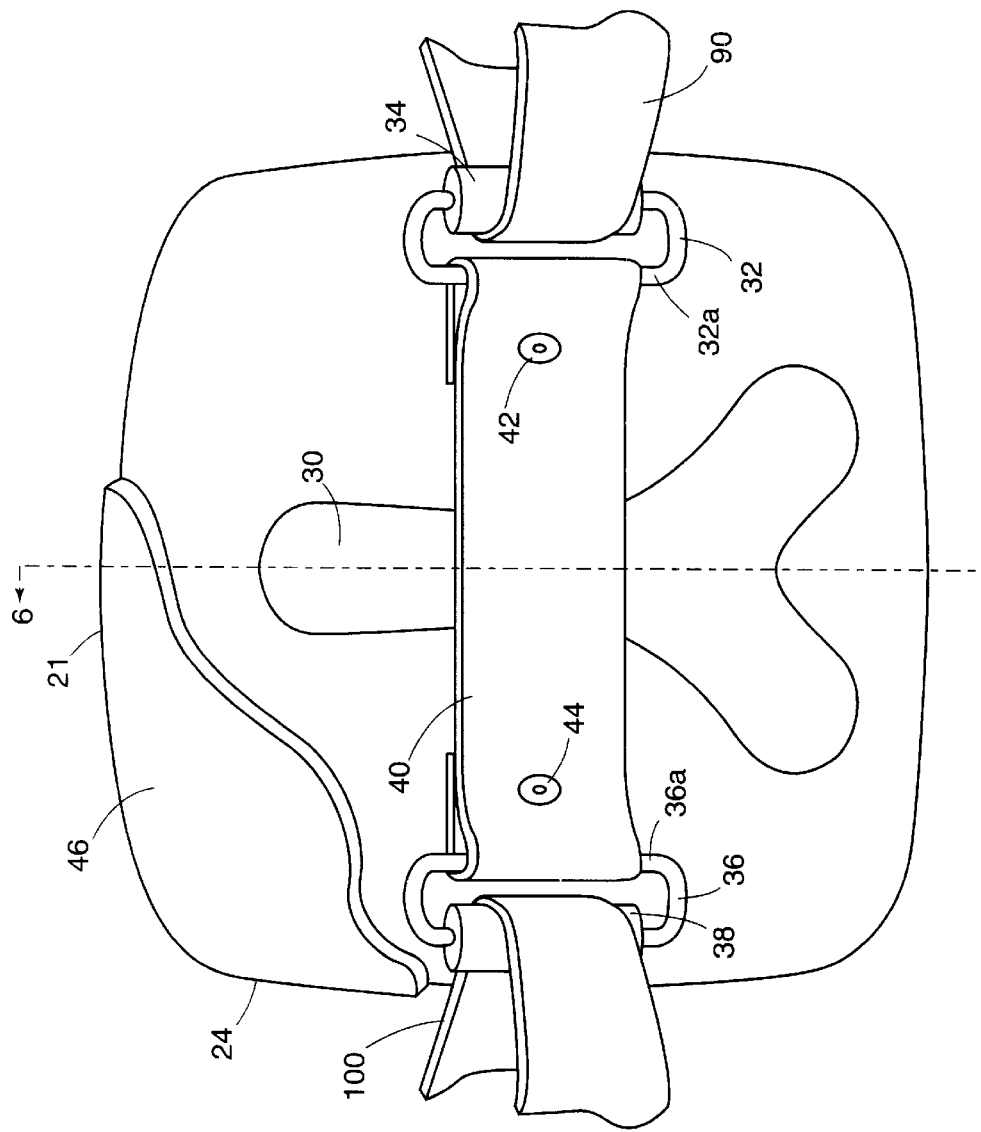
FIG. 5 is an enlarged rear view of the lumbar support section, partially broken away for simplicity.

As is best shown in FIGS. 1, 5 and 6, lumbar support section 20 of brace 10 includes a lumbar support member 26 surrounded by casing 46, which is made, as an example, of a closed cell foam material to provide for comfortable wearing. Lumbar support section 20 is contoured to fit snuggly against the wearer's lumbosacral region and is generally defined by a curved upper edge 21, a similarly curved lower edge 22, and first and second lateral edges 23 and 24, which join upper edge 21 and lower edge 22. Lateral edges 23 and 24 preferably extend around the sides of the wearer so that lumbar support section 20 will generally spacially accommodate the wearer's lumbosacral region.

Referring to FIG. 6, lumbar support member 26 is shown in cross-section and is illustrated as having an undulating profile to be vertically contoured to the wearer's lumbosacral region, with its upper portion tending to curve away from the wearer's lower back, allowing for some flexibility to the wearer when the brace is fully compressed about his or her mid-section. Lumbar support member 26 is preferably made of a laminate material having an outer plate 27 attached to a generally soft pliable inner layer 28, which outer plate 27 is preferably formed by molding of a strong, rigid plastic material. Additionally, as best shown in FIG. 5, lumbar support member 26 preferably has defined a raised vertical protrusion 30 centered thereon and extending inwardly towards the lumbar spine of the wearer. Protrusion 30 is splayed in an inverted V-shape towards the bottom to ensure proper placement of the lumbar support section. As such, protrusion 30 is designed to help center lumbar support section 20 over the wearer's lumbosacral area for optimal support and effectiveness.

As shown in FIGS. 1 and 5, first and second lumbar support D-rings 32 and 36 are fixed to lumbar support member 26 by strap 40. Strap 40 is wrapped around legs 32a and 36a of D-rings 32 and 36, respectively, and then doubled back upon itself and attached to abdominal support member 26 by fasteners 42 and 44, which are preferably metal rivets. First and second lumbar support D-rings 32 and 34 are preferably made of a strong, non-resilient metal such as steel, although foreseeable some new polymeric or other synthetic material yet developed may suffice. Alternatively, tubular bearings 34 and 38 can be rotatably mounted on D-rings 32 and 36, respectively, to provide anti-friction properties to D-rings 32 and 36, thereby decreasing the force necessary to cinch the brace, as is more fully explained below.

Casing 46 envelopes the lumbar support member 26, D-rings 32 and 36 and strap 40 in such manner as to completely cover the D-rings without impairing their function. Casing 46 includes slots 48 and 49 so that straps 90 and 100 can pass through casing 46 to be threaded through D-rings 32 and 36, as is explained below.

Abdominal support pad 51 is generally contoured to be fitably worn over the abdominal region of the wearer and functions as an abdominal support member. Abdominal support pad 51 generally consists of an anterior surface 52 and a posterior surface 53, which are stitched together to form a pouch 57 for optionally receiving abdominal stiffener member 58, and also includes first and second lateral edges 54 and 56, respectively. As such, abdominal support pad 51 is a pouch member which, as shown below, can receive stiffener members to provide additional support to the wearer.

As shown in FIG. 3, D-ring 60 is fixed to abdominal support pad posterior surface 53 by strap 64, which is wrapped around leg 60a of D-ring 60, and is then doubled back upon itself and is attached to posterior surface 53 by sewing or other accepted method of attachment. D-ring 60 is preferably made of a strong, non-resilient metal, such as steel. Alternatively, tubular bearing 62 can be rotatably mounted on D-ring 60 to provide anti-friction properties to D-ring 60, thereby decreasing the force necessary to cinch the brace, as is more fully described below. Patch 66 is sewn or otherwise firmly attached to posterior surface 53 in such manner as to completely cover D-ring 60 without impairing the function thereof. Edge 66a of patch 66 is not attached to posterior surface 53, thereby creating slot 66b.

Anterior surface 52 of abdominal support pad 51 is preferably made of a soft fabric material, such as closed cell foam, similar to casing 46, to provide for comfortable wearing. Of course, other materials can be substituted, such as a waterproof covering, at least temporarily, if necessary.

As is more fully explained below, posterior surface 53 will mate with fastening patch 75 of abdominal support band 70, thus forming the abdominal support system 50. Accordingly, posterior surface 53, like abdominal support band posterior surface 73, is preferably made of a flexible, non-elastic material that will allow for detachable fastening with hook and loop-type material.

Abdominal stiffener 58 is preferably formed of a thermoplastic material and is shaped to generally fit within pouch 57. Varying shapes and sizes can be utilized depending upon the wearer's need for support and desire for comfort. It is preferred that a great number of stiffeners of varying rigidity will be provided with support brace 10 to be interchangeably worn within pouch 57, depending upon the wearer's needs, to place compressive forces on the wearer's abdominal cavity.

Abdominal support band 70 consists generally of a fixed end 72 and distal end 71, and is attached at fixed end 72 to lumbar support second lateral edge 24. Abdominal support band 70 is a band member preferably made of a flexible elastic material. As shown in FIGS. 1 and 2, fastener patch 75 is fixed to the underside of distal end 71 by stitching or other acceptable method of attachment. Preferably, fastener patch 75 is made of a hook and loop-type material for detachably fastening to abdominal support pad posterior surface 53. Posterior surface 73 is attached to the opposite side of distal end 71 from fastener patch 75 by stitching or other acceptable fastening method. Preferably, posterior surface 73 is made of a flexible, non-elastic fabric material that will allow for detachable fastening with hook and loop material.

Loop 79 is preferably made of nylon or other non-elastic high strength fiber, and is fixed to distal end 71 as shown best in FIG. 4. Loop 79 can be used by the wearer to pull abdominal support band 70 around the left side of the wearer to detachably fasten to abdominal support pad 51, as is explained in greater detail below.

D-ring 77 is fixed to distal end 71 by strap 76, which is wrapped around leg 77a of D-ring 77, and is then doubled back upon itself and is attached to posterior surface 73 by stitching or other acceptable means of attachment. D-ring 77, like D-rings 32, 36 and 60, is preferably made of a high strength, non-resilient metal, such as steel. Alternatively, tubular bearing 78 can be rotatably mounted on D-ring 77 to provide anti-friction properties to D-ring 77, thereby decreasing the force necessary to cinch the brace, as is more fully described below. Patch 74 is sewn or otherwise attached to posterior surface 75 in such manner as to completely cover D-ring 77 without impairing the function thereof. Edge 74a of patch 74 is not attached to posterior surface 73, thereby creating slot 74b. Patch 74, like posterior surface 73, is preferably made of a flexible, non-elastic material that will allow for detachable fastening with hook and loop-type material.

D-rings 32, 36, 60 and 77 are preferably, but not necessarily, in the general shape of a rectangle as shown in FIGS. 1, 3–5. Additionally, the D-rings 32, 36, 60 and 77 have a round cross-section, to allow bearings 34, 38, 62 and 78 to rotate freely about D-rings 32, 36, 60 and 77, respectively. Importantly, all D-rings 32, 36, 60 and 77 are preferably completely covered, as shown and described, to thereby prevent the wearer of brace 10 from purposefully or inadvertently altering the connections to such D-rings. Covering of the D-rings also provides: (1) improved wearer comfort over known braces, as the metal rings do not touch the wearer; and (2) improved safety and ease of use, as the covered D-rings cannot catch on furniture, articles of clothing or other objects.

Strap 90 is preferably fixably attached at fixed end 92 to lumbar support first lateral edge 23. Free end 94 of strap 90 is first passed through slot 66b and then threaded through abdominal support pad D-ring 60 from the back of D-ring 60 toward the front of D-ring 60 so that it loops around D-ring bearing 62. Free end 94 is then passed again through slot 66b, turned back upon itself and passed through first casing slot 48. Free end 94 is then threaded through lumbar support first D-ring 32 from the back of D-ring 32 towards the front of D-ring 32, so that it loops around D-ring bearing 34. Thereafter, free end 94 is passed back through casing slot 48.

Strap 100 is preferably fixably attached at a fixed end 102 thereof to lumbar support second lateral edge 24. Free end 104 is first passed through slot 74b of abdominal support band 70 and then threaded through abdominal support band D-ring 77, from the back of D-ring 77, towards the front of D-ring 77, so that it loops around D-ring bearing 78. Free end 104 is then passed back through slot 74b, turned back upon itself and passed through second casing slot 49 of lumbar support section 20. Free end 104 is then threaded through lumbar support second D-ring 36 from the back of D-ring 36 towards the front of D-ring 36 so that it loops around D-ring bearing 38. Thereafter, free end 104 is passed back through casing slot 49.

As shown in FIG. 2, free ends 94 and 104 may be provided on their underside with hook and loop type material sections 98 and 108, respectively, for selectively attaching to posterior surface 53, patch 74 and/or posterior surface 73. Similarly, as shown in FIG. 1, free ends 94 and 104 may be provided on their topsides with hook and loop type material section 96 and 106, respectively, for selectively attaching to the underside hook and loop material sections of the opposite strap.

Straps 90 and 100 are preferably made of a flexible woven fabric such as, by example, an inelastic nylon or other high strength fiber. Other materials can be suitably substituted so long as the product is flexible but generally inelastic.

Band 80 is fixably attached to lumbar support first lateral edge 23 at one end and to abdominal support first lateral edge 54 at the other end by stitching or other suitable fastening method. Band 80 maintains abdominal support pad 51 and lumbar support section 20 in a spaced apart relation to one another when brace 10 is placed about the mid-section of a wearer and increases the ease with which to don the brace. Abdominal support band 70 and band 80 are preferably made of an elastic material so that the spaced apart relation of lumbar support section 20 and abdominal support pad 51 can be expanded depending upon the girth of the wearer. Additionally, the elasticity of band 80 and abdominal support band 70 allow the wearer to selectively compress brace 10 when abdominal support pad 51 is placed over the wearer's abdominal region and support band 70 is wrapped around the wearer's left side, and joining fastening patch 75 to anterior surface 53 in a multitude of locations. This mode of wearing the brace 10 is more fully described below.

Figure 7:
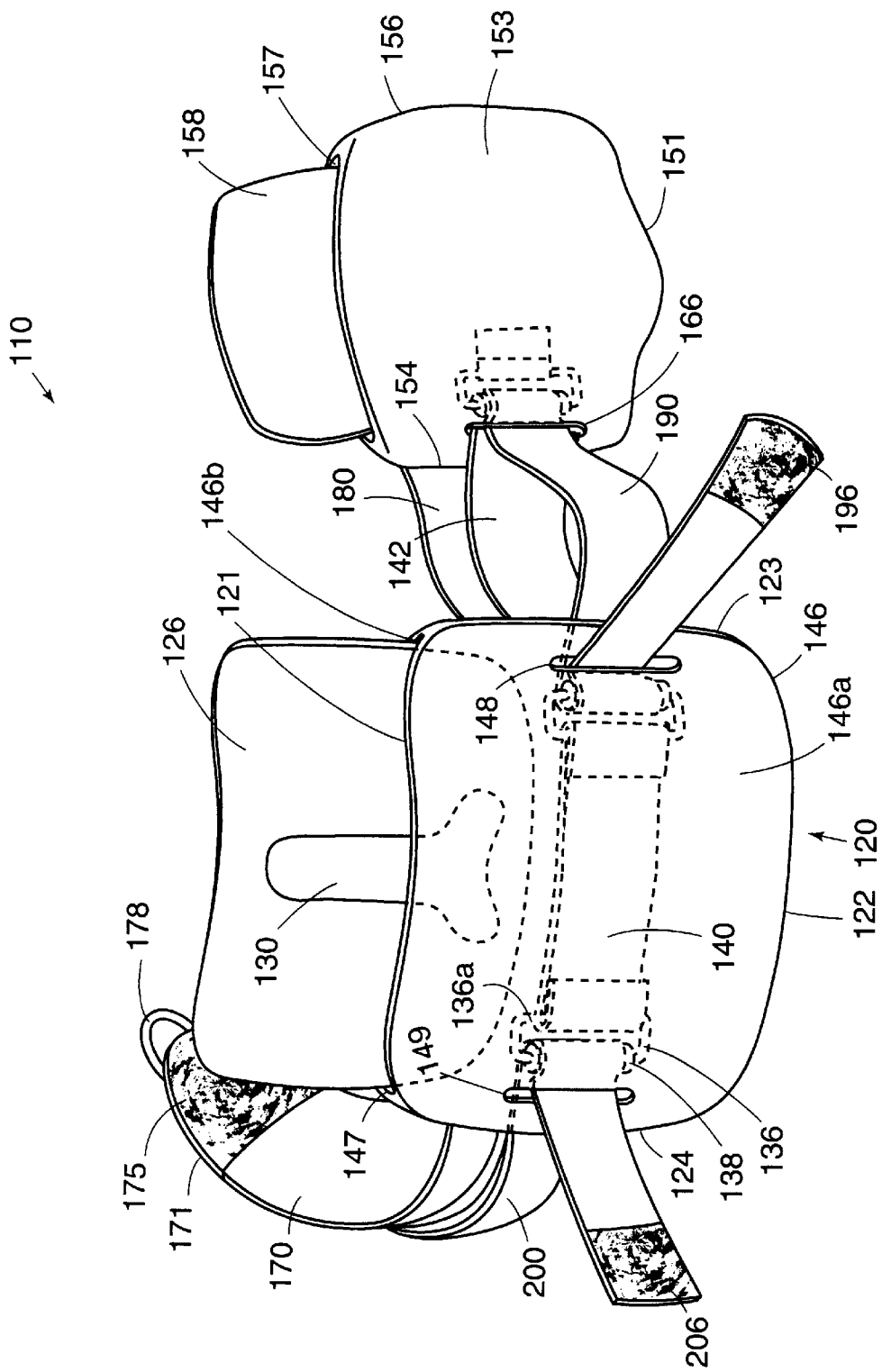
FIG. 7 is a rear perspective view illustrating an alternative embodiment of the support brace, shown open and having a lumbar support member extending from the casing of the lumbar support section. Certain hidden features are shown in phantom.
Figure 8:
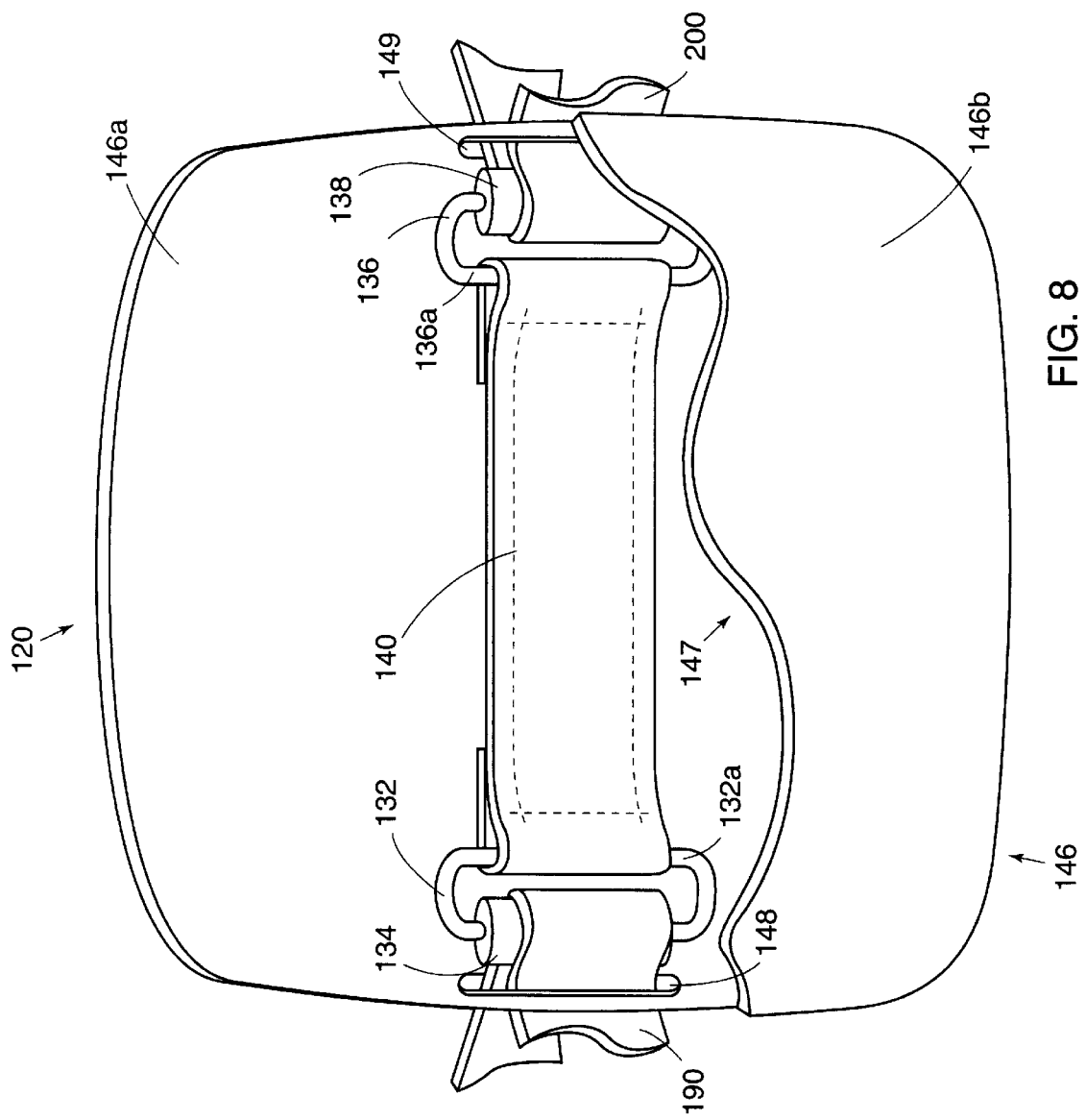
FIG. 8 is an enlarged front view of the alternative embodiment of the lumbar support section of FIG. 7, partially broken away for simplicity.
Figure 9:
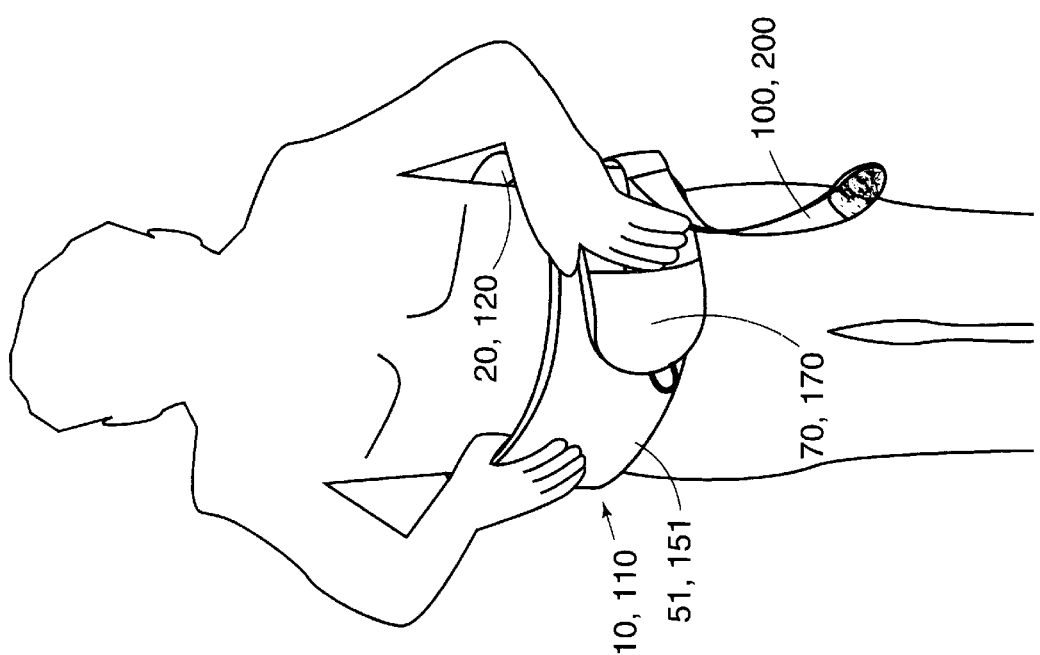
FIG. 9 is a schematic view showing the braces of FIGS. 1 and 7 being attached to the wearer.

An alternative embodiment of the present invention is illustrated in FIGS. 7, 8 and 9. Unless otherwise specified herein, aspects of the second embodiment function in the same manner as the first embodiment, described above. Brace 110, which has been labeled with the same reference numbers as brace 10, plus 100, is identical to brace 10, except that the lumbar support section 120 has been reconfigured to provide the wearer greater flexibility in using the brace 110. Specifically, D-rings 132 and 136 have been attached to casing 146 of lumbar support section 120 instead of being fixed to lumbar support member 126.

In this second embodiment, lumbar support section 120 includes a lumbar support member 126 and a casing 146, which is generally defined by upper edge 121, lower edge 122 and first and second lateral edges 123 and 124, respectively. Casing 146 generally consists of posterior member 146a and anterior member 146b which are made, as an example, of a close cell foam material to provide for comfortable wearing, and are fixed together on lower edge 122, and first and second lateral edges 123 and 124, respectively, by stitching or other acceptable means to form pouch 147 for receiving lumbar support member 126. As such, casing 146 is a pouch member which, as shown below, receives lumbar support member 126 to provide customized support to the wearer. Casing 146 is contoured to adapt to the general shape of the wearer's lumbosacral region, and first and second lateral edges 123 and 124 preferably extend around the sides of the wearer so that lumbar support section 120 will generally spacially accommodate the wearer's lumbosacral region.

As shown in FIGS. 7 and 8, first and second lumbar support D-rings 132 and 136 are fixed to the inner surface of posterior member 146a by strap 140, by stitching or other acceptable method of attachment. Accordingly, when brace 110 is donned by the wearer, D-rings 132 and 136 are located totally within pouch 147, thereby precluding the D-rings from being snagged by the wearer's clothing or other item. D-rings 132 and 136 are concealed within pouch 147 of casing 146 so as not to impair the function of the D-rings.

Strap 140 is wrapped around legs 132a and 136a of D-rings 132 and 136, respectively, and then doubled back and attached to itself by stitching or other acceptable method of attachment. First and second lumbar support D-rings 132 and 136 are preferably made of a strong, non-resilient metal such as steel, although forseeable some new polymeric or other synthetic material yet developed may suffice. The D-rings 132 and 136 preferably have a rounded cross-section, and alternatively, tubular bearings 134 and 138 can be rotatably mounted on D-rings 132 and 136, respectively, to provide anti-friction properties to D-rings 132 and 136, thereby decreasing the force necessary to cinch the brace, as explained above.

Posterior member 146a includes slots 148 and 149 so that straps 190 and 200 can pass through casing posterior member 146a to be threaded through D-rings 132 and 136, as explained below.

As noted above, D-rings 132 and 136 are preferably completely covered, as shown and described, to thereby prevent the wearer of brace 110 from purposely or inadvertently altering the connections to such D-rings. Covering the D-rings also provides improved wearer comfort over known braces and improves safety and ease of use.

Lumbar support member 126, like lumbar support member 26, preferably has defined a raised vertical protrusion 130, centered thereon and extending inwardly towards the lumbar spine of the wearer, that is splayed in an inverted V-shape towards the bottom to ensure proper placement of the lumbar support section. As such, protrusion 130 is designed to help center lumbar support section 120 over the wearer's lumbosacral area for optimal support and effectiveness. As noted above, lumber support member 126 is removably received within pouch 147 of casing 146.

One advantage of attaching the lumbar support D-rings to casing 146, as opposed to lumbar support member 126, is that the wearer may remove lumbar support member 126 to wash or otherwise clean brace 110. Additionally, this second embodiment allows the manufacturer to alter the size, shape and stiffness of the lumbar support member 126 to accommodate the wearer's anatomy and clinical needs, thereby further ensuring patient compliance with wearing requirements.

The brace 10, 110 is donned by placing lumbar support section 20, 120 against the lumbosacral region of the wearer as shown in FIG. 9. Thereafter, abdominal support pad 51, 151 is wrapped forwarded around the right side of the wearer and positioned over the wearer's abdomen. The abdominal support band 70, 170 is then wrapped around the left side of the wearer toward the wearer's front. Distal end 71, 171 is then overlapped onto the abdominal support pad anterior surface 53, 153 and is adjustably fastened thereto by fastener patch 75, 175. Loop 78, 178, secured to distal end 71, 171, can be used by the wearer to assist in pulling abdominal support band 70, 170 into position to be joined to abdominal support pad 51, 151. In that support band 70, 170 is preferably made of an elastic material, it can be pulled with a selected amount of force so as to compress lumbar support section 20, 120 to the wearer's lumbosacral region, and can be selectively adjustably fastened (or released) by attaching abdominal support band 70, 170 to abdominal support pad 51, 151 in a variety of positions.

After the abdominal support band 70, 170 and abdominal support pad 51, 151 are so joined, the wearer grasps fastening strap fastening distal ends 94, 194 and 104, 204 and pulls the straps in a forward direction, which in turn pulls the lumbar support section lateral edges 23, 123 and 24, 124 towards abdominal support pad lateral edges 54, 154 and 56, 156 respectively, thereby cinching and compressing the brace around the wearer's mid-section.

In view of the foregoing, it will be seen that the several objects of the inventions are achieved and other advantages are attained. Although the foregoing includes a description of the best mode contemplated for carrying out the invention, various modifications are contemplated.

As various modifications could be made in the constructions herein described and illustrated without departing from the scope of the invention, it is intended that all matter contained in the foregoing description and shown in the accompanying drawings shall be interpreted as illustrative rather than limiting.

What is claimed is:

1. A support brace comprising:
   a lumbar support section having first and second lateral edges, and first and second D-rings fixed to said lumbar support section;
   an abdominal support pad connected to said lumbar support section first lateral edge, and having a third D-ring fixed to said abdominal support pad;
   an abdominal support band connected to said lumbar support section second lateral edge, having a distal end adapted for detachable fastening to said abdominal support section, and a fourth D-ring fixed to said abdominal support band;
   a first strap having a fixed end and a free end, said first strap fixed end attached to said lumbar support section first lateral edge, and said first strap free end threadably engaging said abdominal support pad third D-ring and then successively threadably engaging said lumbar support section first D-ring, wherein said free end of said first strap projects from said lumbar support section first D-ring; and
   a second strap having a fixed end and a free end, said second strap fixed end attached to said lumbar support section second lateral edge, and said second strap free end threadably engaging said abdominal support band fourth D-ring and then successively threadably engaging said lumbar support section second D-ring, wherein said free end of said second strap projects from the lumbar support section second D-ring;
   whereby said brace can be selectively tightened by pulling on said free ends of said first and second straps.

2. The support brace of claim 1, wherein said lumbar support section further comprises a laminate member having a generally stiff contoured outer plate adjacent to a generally soft pliable inner layer.

3. The support brace of claim 2, wherein said laminate member is enclosed in a casing made of a soft pliable material to provide cushioning for comfortable wearing.

4. The support brace of claim 3, wherein said abdominal support band and said abdominal support pad are fastened to said casing.

5. The support brace of claim 3, wherein said first and second straps are fastened to said casing.

6. The support brace of claim 1, wherein said lumbar support section is generally contoured to fit about the wearer's lumbosacral region.

7. The support brace of claim 2, wherein said laminate member includes a vertical raised protrusion extending inwardly and having a top and a bottom, with an inverted V-shaped section at said bottom, sized and positioned appropriately for fitting over a wearer's lumbosacral region.

8. The support brace of claim 2, wherein said first and second D-rings of said lumbar support section are fixed to said outer plate of said laminate member.

9. The support brace of claim 3, wherein said first and second D-rings of said lumbar support section are fixed to said casing.

10. The support brace of claim 1, wherein said abdominal support pad has an anterior surface made of soft pliable fabric cushioning material, and a posterior surface made of hook and loop type material for selective fastening said abdominal support pad to said abdominal support band.

11. The support brace of claim 1, wherein said abdominal support pad comprises an anterior surface and a posterior surface that are connected together in such a manner as to define a pouch, and a stiffener member selectively deposited in said pouch to provide added support to the wearer.

12. The support brace of claim 11, wherein said stiffener member is shaped to generally conform to the wearer's abdominal region and is made of thermoplastic material.

13. The support brace of claim 11, wherein a plurality of stiffener members with varying degrees of rigidity can be provided to alter the amount of support provided to the wearer.

14. The support brace of claim 1, wherein the abdominal support pad is shaped to generally conform to the wearer's abdominal region.

15. The support brace of claim 10, wherein said anterior surface of said abdominal support pad is made of a soft, pliable material to provide for comfortable wearing.

16. The support brace of claim 1, wherein said first and second straps are made of a generally flexible, inelastic material.

17. The support brace of claim 1, wherein said free ends of said first and second straps include hook and loop type fastener material for detachably engaging to said abdominal support pad and said abdominal support band.

18. The support brace of claim 1, wherein said abdominal support band is elastically connected to said lumbar support section.

19. The support brace of claim 1, wherein said abdominal support band distal end has an anterior and a posterior surface, said anterior surface being detachably fastenable to said abdominal support pad, and said posterior surface detachably engaging said free ends of said first and second straps.

20. The support brace of claim 1, wherein said abdominal support band distal end further comprises a loop of flexible, inelastic material to aid in the donning of said support brace.

21. The support brace of claim 1, wherein said first, second, third and fourth D-rings are covered with material in such manner as to completely cover said D-rings without impairing the function thereof, thereby preventing contact of said D-rings to the wearer's skin and precluding entanglement of said D-rings.

22. A support brace comprising:
a lumbar support section having first and second lateral edges, a laminate member having an outer plate and an inner layer, said outer plate having first and second D-rings fixed to said outer plate;
an abdominal support system having an abdominal support pad and an abdominal support band, said abdominal support pad having first and second lateral edges and an anterior and posterior surface, said posterior surface having a third D-ring fixed to said posterior surface of said abdominal support pad, said abdominal support band having fixed and distal ends, said distal end having hook and loop type fastener material, said hook and loop type fastener material being detachably connected to said abdominal support pad, said fixed end attached to said lumbar support section second lateral edge, and further having a fourth D-ring fixed to said distal end;
a band connecting said lumbar support section first lateral edge and said abdominal support pad first lateral edge, said band maintaining said lumbar support section first lateral edge and said abdominal support pad first lateral edge in a spaced apart relationship;
first and second straps, each having a fixed and a free end, wherein said first strap fixed end fixably attached to said lumbar support section first lateral edge, said first strap free end engaging said abdominal support pad third D-ring and then successively threadably engaging said lumbar support section first D-ring, said second strap fixed end being fixably attached to said lumbar support section second lateral edge, said second strap free end engaging said abdominal support band fourth D-ring and then successively threadably engaging said lumbar support section second D-ring,
whereby the brace is selectively tightened by pulling said free ends.

23. The support brace of claim 22, wherein said abdominal support band distal end has an anterior and a posterior surface, said hook and loop type fastener material of said abdominal support band distal end being proximately located on said anterior and said posterior surface, thereby said anterior surface being detachably fastenable to said abdominal support pad, and said posterior surface detachably receivably engaging said free ends of said first and second straps.

24. An abdominal and lumbar support brace comprising:
a lumbar support section having first and second lateral edges and first and second D-rings fixed to said lumbar support section;
an abdominal support pad having first and second lateral edges and a third D-ring fixed to said abdominal support pad;
an elastic band having a proximal end and a distal end, said proximal end attached to said lumbar support section first lateral edge, said distal end attached to said abdominal support pad first lateral edge, thereby connecting said lumbar support section and said abdominal support pad in a spaced apart relationship;
an abdominal support band having fixed and distal ends, said fixed end attached to said lumbar support section second lateral edge, said distal end having a fourth D-ring fixed to said distal end of said abdominal support band and material for selectively fastening said abdominal support band to said abdominal support pad; and
a tightening means comprising first and second straps independently connected to said lumbar support section first and second lateral edges, respectively, said first strap having fixed and free ends, said first strap free end engaging said abdominal support pad third D-ring and then successively threadably engaging said lumbar support section first D-ring, said first strap fixed end being attached to said lumbar support section first lateral edge, said second strap having fixed and free ends, said second strap free end engaging said abdominal support band distal end fourth D-ring and then successively threadably engaging said lumbar support section second D-ring, said second strap fixed end being attached to said lumbar support section second lateral edge, wherein said abdominal and lumbar support brace is selectively tightened by pulling on said free ends of said first and second straps.

25. An abdominal and lumbar support brace comprising:
a lumbar support section having first and second lateral edges, and further having first and second D-rings attached to said lumbar support section;
an abdominal support system, having an abdominal support pad with first and second lateral edges and an elastic abdominal support band, said abdominal support pad having a third D-ring attached to said abdominal support pad, and said elastic abdominal support band having a fourth D-ring attached to said abdominal support band;

an elastic band having proximal and distal ends, said proximal end extending from said lumbar support section first lateral edge and said distal end extending from said abdominal support pad first lateral edge, thereby connecting said lumbar support section and said abdominal support pad in a spaced apart relationship; and first and second straps with fixed and free ends, said fixed ends of said first and second straps being independently connected to said lumbar support section first and second lateral edges, respectively, said first strap free end engaging said abdominal support pad third D-ring and then successively threadably engaging said lumbar support section first D-ring, and said second strap free end engaging said abdominal support band fourth D-ring and then successively threadably engaging said lumbar support section second D-ring, wherein said abdominal and lumbar support brace is selectively tightened by pulling on said free ends of said first and second straps.

26. A brace tightening device comprising:

a lumbar support member having first and second D-rings fixed to said lumbar support member;

an abdominal support system having a pad member and a band member, said pad member having a third D-ring fixed to said pad member, said band member having a fourth D-ring fixed to said band member;

a first strap having fixed and free ends, said first strap fixed end attached to said lumbar support member, said first strap free end threadably engaging said abdominal support system pad member third D-ring and then successively threadably engaging said lumbar support member first D-ring;

a second strap having fixed and free ends, said second strap fixed end attached to said lumbar support member, said second strap free end threadably engaging said abdominal support system band member fourth D-ring and then successively threadably engaging said lumbar support member second D-ring;

whereby pulling said free ends of said first and second straps causes a tightening of said lumbar support member and said abdominal support system.

27. A method of permitting a person to tighten and compress a support brace, without the assistance of others comprising the steps:

(a) providing a lumbar support section having first and second lateral edges and first and second D-rings fixed to said lumbar support section, a first strap having fixed and free ends, said first strap fixed end attached to said lumbar support section first lateral edge, and a second strap having fixed and free ends, said second strap fixed end attached to said lumbar support section second lateral edge;

(b) providing an abdominal support system, having an abdominal support member and a band member, said abdominal support member and said band member each having a D-ring attached thereto, said band member having a distal end adapted for detachably fastening to said abdominal support member;

(c) threading said first strap free end through said abdominal support member D-ring and then through said lumbar support section first D-ring, wherein said first strap free end projects from said lumbar support section first D-ring;

(d) threading said second strap free end through said band member D-ring and then through said lumbar support section second D-ring, wherein said second strap free end projects from said lumbar support section second D-ring;

(e) placing said lumbar support section against the said person's lumbosacral region, wrapping said abdominal support member forward around one side of said person toward the person's front, wrapping said band member forward around the opposite side of the person toward said person's front and overlapping said band member distal end onto said abdominal support member and fastening it thereto; and (f) grasping said free ends of said first and second straps and pulling said free ends in a forward direction in relation to said person.

* * * * *